United States Patent [19]

Simpkins et al.

[11] Patent Number: 4,786,647
[45] Date of Patent: Nov. 22, 1988

[54] METHOD FOR ELICITING ANXIOLYSIS

[75] Inventors: James W. Simpkins; Warren C. Stern, both of Gainesville, Fla.

[73] Assignees: University of Florida, Gainesville, Fla. ; by said James W. Simpkins; Pharmatec, Inc., Alachua, Fla. ; by said Warren C. Stern

[21] Appl. No.: 879,944

[22] Filed: Jun. 30, 1986

[51] Int. Cl.$^4$ ............................................. A61K 31/44
[52] U.S. Cl. ................................................... 514/355
[58] Field of Search ........................................ 514/355

[56] References Cited

PUBLICATIONS

Chem. Abst. 96-193953(b) (1982).
Chem. Abst. 104-122325(w) (1986).
*Goodman and Gilman's The Pharmacological Basis of Therapeutics*, Sixth Edition, ed. A. G. Gilman et al, MacMillan Publishing Co., Inc., New York 1980, Chapter 19, pp. 436-447.
D. J. Sanger et al, in *L.E.R.S.*, vol. 4, ed. G. Bartholini et al, Raven Press, New York, 1986, pp. 77-84.
M. G. Corda et al, in *GABAergic Transmission and Anxiety*, ed. G. Biggio et al, Raven Press, New York, 1986, pp. 121-136.
J.-Y. Wu et al, in *GABAergic Transmission and Anxiety*, ed. G. Biggio et al, Raven Press, New York, 1986, pp. 161-176.
C. Martini et al, in *GABAergic Transmission and Anxiety*, ed. G. Biggio et al, Raven Press, New York, 1986, pp. 1-10.
G. Bartholini et al, in *L.E.R.S.*, vol. 3, ed. G. Bartholini et al, Raven Press, New York, 1985, pp. 1-30.
D. N. Stephens et al, in *GABAergic Transmission and Anxiety*, ed. G. Biggio et al, Raven Press, New York, 1986, pp. 91-106.
R. W. Olsen et al, in *GABAergic Transmission and Anxiety*, ed. G. Biggio et al, Raven Press, New York, 1986, pp. 21-32.
T. Lempérière et al, in *L.E.R.S.*, vol. 4, ed. G. Bartholini et al, Raven Press, New York, 1986, pp. 161-162.
M. Toscana Aguilar et al, in *L.E.R.S.*, vol. 4, ed. G. Bartholini et al, Raven Press, New York, 1986, pp. 167-168.
R. Volmat et al, in *L.E.R.S.*, vol. 4, ed. G. Bartholini et al, Raven Press, New York, 1986, pp. 169-170.
F. G. Graeff et al, in *L.E.R.S.*, vol. 4, ed. G. Bartholini et al, Raven Press, New York, 1986, p. 101.
A. Guidotti et al, in *L.E.R.S.*, vol. 3, ed. G. Bartholini et al, Raven Press, New York, 1985, pp. 31-41.
G. Bartholini, in *L.E.R.S.*, vol. 4, ed. G. Bartholini et al, Raven Press, New York, 1986, pp. 1-7.
Worms et al, *J. Pharmacol. Exp. Ther.*, vol. 220, No. 3, pp. 660-671 (1982).

*Primary Examiner*—Stanley J. Friedman
*Attorney, Agent, or Firm*—Mary Katherine Baumeister; Dennis P. Clarke

[57] ABSTRACT

The invention provides a method for relieving anxiety in a mammal using a compound of the formula

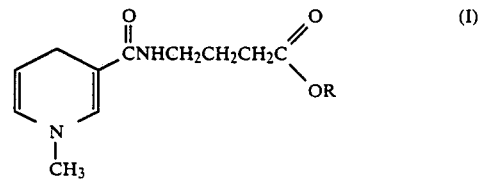

wherein R is Benzyl or cyclohexyl, or a non-toxic pharmaceutically acceptable salt thereof. A preferred compound for use in the subject method is 1-methyl-3-{N-[(3'-benzyloxycarbonyl)propyl]}carbamoyl-1,4-dihydropyridine.

4 Claims, 3 Drawing Sheets

METHOD FOR ELICITING ANXIOLYSIS

FIELD OF THE INVENTION

The present invention relates to the use of selected brain-specific dihydropyridine redox carrier type derivatives of γ-aminobutyric acid in the treatment of anxiety in mammals.

BACKGROUND OF THE INVENTION

Recently, a chemical delivery system (CDS) has been devised which promises to deliver centrally acting drugs to the brain in a site-specific and sustained manner. In accord with this system, the desired central effects of drugs can be achieved without the high concentrations throughout the body which are believed to be responsible for the significant toxic effects typically associated with the drugs. Moreover, this system allows delivery to the brain of drugs which are not themselves capable of passing the blood-brain barrier (BBB).

The drug delivery system referred to above and its applicability to γ-aminobutyric acid (GABA) is generally described in Bodor U.S. Pat. No. 4,479,932 issued to UNIVERSITY OF FLORIDA on Oct. 30, 1984, and more specifically in UNIVERSITY OF FLORIDA's International Application No. PCT/US83/00725 (published under International Publication No. WO 83/03968), in Bodor U.S. Pat. No. 4,540,564 issued to UNIVERSITY OF FLORIDA on Sept. 10, 1985, and in copending Bodor U.S. patent application Ser. No. 665,940, filed Oct. 29, 1984. Briefly, according to the GABA-CDS system, the target drug is tethered to a reduced, blood-brain barrier penetrating lipoidal form of a dihydropyridine⇌pyridinium salt type redox carrier. Oxidation of the dihydropyridine carrier moiety in vivo to the ionic pyridinium salt type carrier/GABA entity prevents elimination thereof from the brain, while elimination from the general circulation is accelerated, and subsequent cleavage of the quaternary carrier/GABA species results in sustained delivery of GABA in the brain and facile elimination of the carrier moity.

In a representative embodiment of the GABA-CDS system, the carboxyl function of GABA is suitably protected to prevent premature metabolism while the trigonelline-type carrier is linked to the drug through GABA's amino function. See in particular the aforementioned U.S. Pat. Nos. 4,479,932, at column 14, line 45 to column 18, line 30; and 4,540,564, at column 37, line 60 to column 41, line 34 and again at column 55, line 1 to column 61; and especially the aforementioned copending U.S. application Ser. No. 665,940, Examples 96–103, which detail preparation of 1-methyl-3{N-[(3'-benzyloxycarbonyl)propyl]}carbamoyl-1,4-dihydropyridine and 1-methyl-3{N-[(3'-cyclohexyloxycarbonyl)propyl]}carbamoyl-1,4-dihydropyridine and intermediates thereto.

As discussed at length in the aforementioned U.S. patents and patent application, the rational of the GAPA/carrier approach derives from the GABA hypothesis of epilepsy. It has been shown that GABA neuron function is impaired in at least certain types of human epilepsy, while animal studies have shown that seizures are induced by reduction of GABA neuron function to a critical degree by (1) inhibition of GABA synthesis, (2) blockade of GABA receptors or (3) inhibition of GABA-receptor mediated ionic events. In addition, enhancement of GABA synaptic activity (by direct receptor stimulation or by increasing GABA levels in the synapse) has a potent and wide spectrum anticonvulsant effect. However, GABA itself, when systemically administered, does not penetrate the normal blood-brain barrier to any significant extent. The GABA-CDS is thus proposed by the aforementioned patent publications as one means of providing for the effective, selective and non-toxic treatment of epilepsy, but no other potential uses of any of the GABA/carrier compounds are disclosed or suggested therein.

Anxiety is a psychological state characterized by apprehension, nervousness, restlessness and the feeling of insecurity about one's future. While anxiety is a well-defined psychological condition, it is extremely difficult to evaluate objectively, particularly since anxiety is a component of several neuroses and psychoses. Additionally, anxiety varies in its intensity. Mild anxiety is described as restlessness, nervousness, uneasiness or anxiousness. More intense anxiety expresses itself as agitation, anxiety attacks, panic attacks or anxiety neurosis. Severe anxiety is a component of neurocirculatory asthenia, hysterical neurosis, hypochondriacal neurosis, obsessive-compulsive neurosis, phobic neurosis and neuroasthenic neurosis.

Anxiety is an integral part of the human response to external conditions. Mild anxiety is often associated with the stress of everyday living and the cause of the anxiety is not well-defined. By contrast, a more severe anxiety is caused by defined life events, i.e. a prospective surgical or medical procedure, marriage, divorce, the death of a family member or friend or the like. In such cases, the anxiety usually wanes as time passes.

Medical conditions and drug use can also cause anxiety. Anxiety is associated with hyperthyroidism and hypercorticosteroidism, as well as with the therapeutic administration of thyroid hormones and glucocorticoids. The changing gonadal steroid environment which causes premenstrual syndrome, post-partum depression and post-menopausal mood changes is frequently associated with anxiety. Anxiety results from the therapeutic use of the β-adrenergic agonist isoproterenol, and the $\alpha_2$-adrenergic antagonists, piperoxane and yohimbine. The use of cocaine and amphetamines or their derivatives causes anxiety and the use of tetrahydrocannabinols causes anxiety, particularly among first-time users. Finally, anxiety is a consistent occurrence in patients experiencing withdrawal from addictive drugs such as nicotine, alcohol, benzodiazepines, barbiturates, opiates, cocaine, tetrahydrocannabinols and their derivatives. Anxiety increases with the intensity of the withdrawal.

Most drugs which are used in the treatment of anxiety are either sedatives or exhibit sedating properties. Even the benzodiazepines, which not only have anticonvulsant/antiepileptic utility but also are the most-widely prescribed anxiolytics, suffer from sedating side effects. Diazepam, for example, produces antianxiety effects at blood concentrations of 400–600 ng/ml, but sedative effects and psychomotor impairment are observed beginning at 300–400 ng/ml. See Goodman and Gilman's The Pharmacological Basis of Therapeutics, sixth edition, ed. A. G. Gilman et al, Macmillan Publishing Co., Inc., New York, 1980, Chapter 19, pp. 436–447.

For many years, little was known about the mechanism of action of the benzodiazepines. However, a large body of evidence now supports the belief that the neurochemical and neuropharmacological actions of the benzodiazepines, including their anxiolytic and sedative effects, may result from their enhancement of GABA-mediated transmission. Benzodiazepines are now thought to increase the affinity of GABA receptors for GABA and to thus facilitate GABAergic transmission. The discovery of this relationship between the benzodiazepines and GABA, and similar discoveries relating to the barbiturates and other GABAergic agents, as well as research on anxiogenic drugs, suggest that the neurotransmitter GABA in involved in the etiology of anxiety. Nevertheless, the hypothesized involvement of GABA in anxiety is controversial. For representative literature in this area, see: D.J. Sanger et al, in L.E.R.S. Volume 4, ed. G. Bartholini et al, Raven Press, New York, 1986, pp. 77–84; M. G. Corda et al, in GABAergic Transmission and Anxiety. ed. G. Biggio et al, Raven Press, New York, 1986, pp. 121–136; J.-Y. Wu et al, in GABAergic Transmission and Anxiety, ed. G. Biggio et al, Raven Press, New York, 1986, pp. 161–176; C. Martini et al, in GABAergic Transmission and Anxiety, ed. G. Biggio et al, Raven Press, New York, 1986, pp. 1–10; G. Bartholini et al, in L.E.R.S. Volume 3, ed. G. Bartholini et al, Raven Press, New York, 1985, pp. 1–30; D. N. Stephens et al, in GABAergic Transmission and Anxiety, ed. G. Biggio et al, Raven Press, New York, 1986, pp. 91–106; and R. W. Olsen et al, in GABAergic Transmission and Anxiety, ed. G. Biggio et al, Raven Press, New York, 1986, pp. 21–32. (The expression "L.E.R.S." used herein is a recognized abbreviation for Laboratories d'Etudes et de Recherches Synthélabo, Paris, France. Volume 3 of the L.E.R.S. monograph series referred to herein is entitled Epilepsy and GABA Receptor Agonists: Basic and Therapeutic Research, while Volume 4 is entitled GABA and Mood Disorders: Experimental and Clinical Research The book GABAergic Transmission and Anxiety referred to herein is Volume 41 of the Advances in Biochemical Psychopharmacology series.)

Recently, a group of specific GABA receptor agonists has been developed which appears to offer a wide range of therapeutic actions. This group of benzylidene-type GABA receptor agonists includes progabide and fengabine. These compounds have been tested for a number of therapeutic applications in a variety of animal and clinical test situations reported in the literature.

Fengabine has been shown to be active in animal models predicting human antidepressant activity. In clinical trials assessing fengabine's effects on depression, somewhat conflicting results on its effects on anxiety have also been reported. T. Lempérière et al, in L.E.R.S. Volume 4, ed. G. Bartholini et al, Raven Press, New York, 1986, pp. 161–162, report that, in a group of ten patients, the Hamilton Rating Scale for Anxiety (HRSA) mean total score decreased, indicating that fengabine was not anxiogenic. M. Toscano Aguilar et al, in L.E.R.S. Volume 4, ed. G. Bartholini et al, Raven Press, New York, 1986, pp. 167–168, report a lower total score on theHamilton anxiety rating scale in a group of ten patients. On the other hand, R. Volmat et al, in L.E.R.S. Volume 4, ed. G. Bartholini et al, Raven Press, New York, 1986, pp. 169–170, indicate that two patients out of eight dropped out of the study because of the appearance of an anxiety state.

The reports are also conflicting as regards progabide, progabide having been found to be active in some anxiolytic tests and inactive in others. Thus, G. Bartholini et al, in L.E.R.S. Volume 3, ed. G. Bartholini et al, Raven Press, New York, 1985, pp. 1–30, state that diazepam and progabide have both been reported to decrease the escape response which is induced by electrical stimulation of periaqueductal gray matter, but that clinical trials have shown minimal anxiolytic properties. In related animal studies, F. G. Graeff et al, in L.E.R.S. Volume 4, ed. G. Bartholini et al, Raven Press, New York, 1986, p. 101, report that microinjection of progabide, benzodiazepines and other GABAergics into the dorsal periaqueductal gray matter (DPAG) in rats whose DPAG is electrically stimulated similarly increase the threshold of stimulation-induced flight. Muscimol, another GABA agonist, has been reported to exhibit anticonvulsant and anxiolytic action, but also causes severe sedation; A. Guidotti et al, in L.E.R.S. Volume 3, ed. G. Bartholini et al, Raven Press, New York, 1985, pp. 31–41. However, G. Bartholini, in L.E.R.S. Volume 4, Raven Press, New York, 1986, pp. 1–7, states that, contrary to what might be expected from animal tests, in clinical studies anxiety states have not been improved by administration of muscimol or progabide; clinical anticonvulsant studies of progabide, in contrast, correlate well with earlier findings of anticonvulsant activity in animals as well as lack of sedating side effects.

A possible explanation for the conflicting reports on progabide's activity in anxiolytic testing is offered by D. J. Sanger et al, in L.E.R.S. Volume 4, ed. G. Bartholini et al, Raven Press, New York, 1986, pp. 77–84. Those authors report that in an aversive brain stimulation study, progabide and diazepam gave similar results, supporting other findings of an anxiolytic response in tests involving electrical stimulation of periaqueductal gray matter. But the authors also report several other behavioral tests in which progabide gave results unlike the benzodiazepines and other anxiolytics. For example, in electroshock punishment procedures in which thirsty rats are shocked for drinking from a water tube, benzodiazepines attenuate the results and this effect is considered predictive of clinical anti-anxiety activity. Progabide, on the other hand, does not give results significantly different from control animals. It would appear that progabide's clinical lack of impressive anxiolytic effects correlates well with the punishment test but not with the tests involving aversive electrical stimulation of periaqueductal gray matter.

GABA itself has been recently reported to act in a similar manner to certain GABA receptor agonists in aversive brain stimulation studies when the drug is injected directly into selected brain regions. Thus, F. G. Graeff et al, in L.E.R.S. Volume 4, ed. G. Bartholini et al, Raven Press, New York, 1986, p. 101, report that in rats electrically stimulated at the dorsal periaqueductal gray matter (DPAG), microinjection into the DPAG of the benzodiazepines chlordiazepoxide and midazolam, of GABA, of progabide and of the barbiturate pentobarbital all result in an increase of the threshold of stimulation-induced flight. G. Bartholini et al, in L.E.R.S. Volume 3, ed. G. Bartholini et al, Raven Press, New York, 1985, pp. 1–30, had earlier referred to the finding that ". . . GABA itself injected into the periaqueductal gray matter or the midbrain raphe exhibits an anxiolytic action in aversive situations . . . both progabide and diazepam decrease the escape response induced by electrical stimulation of the periaqueductal gray matter . . . "

SUMMARY AND OBJECTS OF THE INVENTION

One object of the present invention is to provide a new method for eliciting anxiolysis in mammals, particularly in humans, in domestic animals such as dogs, cats and horses and in feed lot animals such as cattle and pigs.

Another object of the present invention is to provide pharmaceutical compositions for use in the treatment of anxiety in mammals.

Yet another object of this invention is to provide a new use for selected brain-specific dihydropyridine redox carrier type derivatives of γ-aminobutyric acid in relieving anxiety in mammals.

Yet another object of this invention is to use selected brain-specific dihydropyridine redox carrier type derivatives of γ-aminobutyric acid to elicit anxiolysis at dosages which do not cause significant sedation.

In accord with the foregoing objects of the invention, there is described herein a novel method for relieving anxiety in a mammal, said method comprising administering to a mammal in need of such treatment an anxiolytically effective amount of a compound of the formula

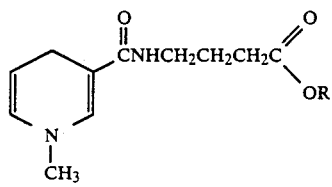

wherein R is benzyl or cyclohexyl, or a non-toxic pharmaceutically acceptable salt thereof. Preferably, the compound employed in the subject method is 1-methyl-3-{N-[(3'-benzyloxycarbonyl)propyl]}carbamoyl-1,4-dihydropyridine, i.e. the compound of formula (1) wherein R is benzyl, or a salt thereof. It is also preferred that the compound of formula (I) or its salt be administered in the form of a pharmaceutical composition comprising an anxiolytically effective amount of the selected active ingredient and a non-toxic pharmaceutically acceptable carrier therefor; and that the dosage of the compound of formula (I) be chosen such that anxiolysis is achieved without significant sedation.

BRIEF DESCRIPTION OF THE DRAWINGS

Other objects and advantages of the present invention will be apparent from the following detailed description and accompanying drawings in which.

Figure 1:
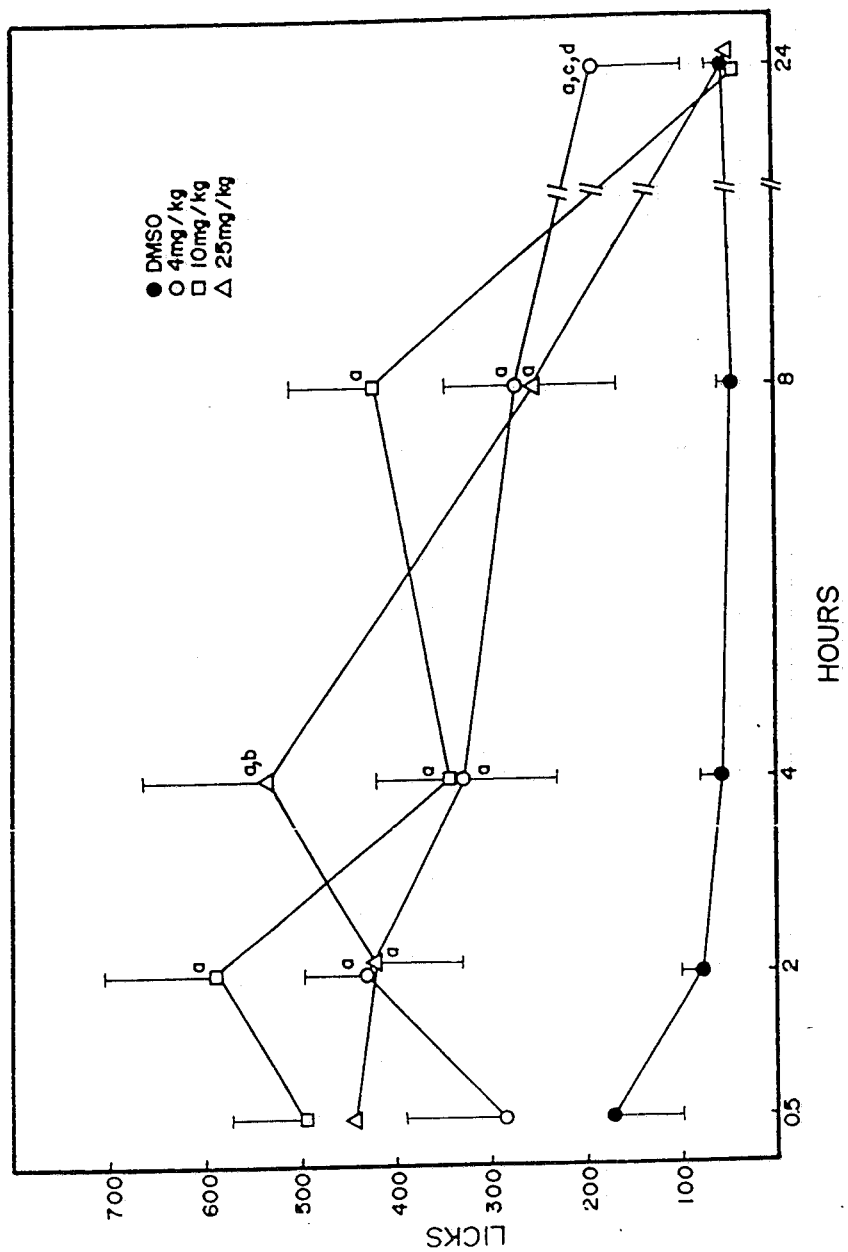
FIG. 1 is a plot of the mean response in number of licks versus time after administration, in a punishment anxiolysis study in groups of rats treated intravenously with dimethylsulfoxide vehicle (●) or with 4 mg/kg (○), 10 mg/kg (□) or 25 mg/kg (△) of 1-methyl-3{N-[(3'-benzyloxycarbonyl)propyl]}carbamoyl-1,4-dihydropyridine (PR-30)

DETAILED DESCRIPTION OF THE INVENTION:

The expression "a non-toxic pharmaceutically acceptable salt" as used herein generally includes the non-toxic salts of the compounds of formula (I) hereinabove formed with non-toxic, pharmaceutically acceptable inorganic or organic acids of the general formula HX. For example, the salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, fumaric, methanesulfonic, toluenesulfonic and the like. The expression "anion of a pharmaceutically acceptable organic or inorganic acid" as used herein, e.g. in connection with formula (II) hereinbelow, is intended to include anions of such HX acids.

It will be appreciated from the foregoing that a compound of formula (I) may be administered as the free base or in the form of a non-toxic pharmaceutically acceptable salt thereof, i.e. a salt which can be represented by the formula

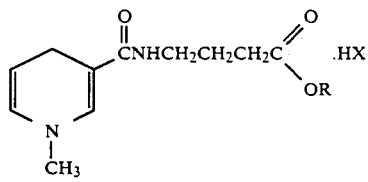

wherein the structural variables are defined as before; and that, regardless of the actual form in which the compound is administered, it will be converted in vivo to a quaternary salt of formula (II) hereinbelow, X⁻ being present in vivo. It is not necessary that the anion be introduced as part of the compound administered. Indeed, even when the compound of formula (I) is used in its salt form, the anion of the formula (II) compound in vivo is not necessarily the same as that present in the formula (I) compound. In fact, the exact identity of the anion portion of the compound of formula (II) is immaterial to the in vivo transformation of (I) to (II).

The compounds of formula (I) which are employed in the method and compositions of the present invention can be synthesized by methods described in the aforementioned Bodor U.S. Pat. Nos. 4,479,932 and 4,540,564, Bodor copending U.S. Ser. No. 665,940 and University of Florida PCT/US3/00725 (International Publication No. W083/03968). Synthesis generally begins with preparation of the corresponding quaternary intermediates of the formula

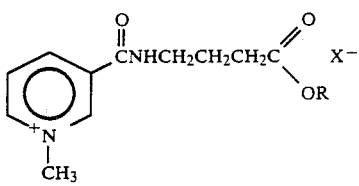

(II)

wherein R is benzyl or cyclohexyl and $X^-$ is the anion of a non-toxic pharmaceutically acceptable organic or inorganic acid. The pyridinium salts of formula (II) are not only chemical intermediates to the corresponding compounds of formula (I), but also represent the form of the chemical delivery system which is "locked in" the brain following administration of the dihydro derivative.

The preparation of the intermediates of formula (II) typically proceeds in three steps, utilizing GABA as the starting material. First, the carboxyl function of GABA is converted to the corresponding benzyl or cyclohexyl ester, e.g. by reaction with the appropriate alcohol in the presence of thionyl chloride. Then, the protected GABA derivative is reacted with nicotinic acid in pyridine in the presence of dicyclohexylcarbodiimide to afford the corresponding N-nicotinoyl derivative. Finally, the N-nicotinoyl derivative is quaternized, e.g. by treatment with methyl iodide in an appropriate solvent, to afford the corresponding formula (II) intermediate. Alternate methods for the preparation of the formula (II) intermediate will be apparent to those skilled in the art, particularly in view of the teachings of the aforementioned Bodor patents and applications.

While the sequence of reaction steps can be varied in many cases, in general the final step (except in the case of optional salt formation) will be reduction of a quaternary compound of formula (II) to the corresponding dihydro compound of formula (I). The reduction is usually conducted at a temperature from about $-10°$ C. to room temperature, for a period of time from about 10 minutes to 2 hours, conveniently at atmospheric pressure. Typically, a large excess of reducing agent is employed, e.g. a 1:5 molar ratio of reducing agent to starting compound of formula (II). The process is conducted in the presence of a suitable reducing agent, preferably an alkali metal dithionite such as sodium dithionite or an alkali metal borohydride such as sodium borohydride or lithium aluminum borohydride, in a suitable solvent. Sodium dithionite reduction is conveniently carried out in an aqueous solution; the dihydro product of formula (I) is usually insoluble in water and thus can be readily separated from the reaction medium. In the case of sodium borohydride reduction, an organic reaction medium is employed, e.g. a lower alkanol such as methanol, an aqueous alkanol or other protic solvent. Sodium dithionite reduction is generally preferred, since it favors production of the desired 1,4-dihydropyridines.

SYNTHETIC EXAMPLES

In order to further illustrate the compounds useful in the method of this invention, the following synthetic examples are given, it being understood that the same are intended only as illustrative.

In the examples immediately to follow, all melting points were taken on a Mel-Temp apparatus and are not corrected. Elemental analyses were performed at Atlantic Microlabs, Inc., Atlanta, Ga.

EXAMPLE 1

Preparation of 4-aminobutanoic acid benzyl ester hydrochloride

GABA (4 g, 38.8 mmol) was suspended in 50 ml (0.48 mol) of benzyl alcohol. The reaction mixture was stirred, with cooling on an ice bath, while 20 ml of $SOCl_2$ was added dropwise over a 30 minute period. The mixture was slowly brought to the reflux temperature and refluxed for 4 hours. The resultant pink viscous solution was cooled to room temperature. Addition of 50 ml of ethyl ether and refrigeration overnight produced white crystals which were collected by filtration, recrystallized from a mixture of ethyl ether and ethanol and dried, m.p. 115°-116° C.

EXAMPLE 2

Preparation of 3{N-[(3'-benzyloxycarbonyl)propyl]}carbamoylpyridine

Nicotinic acid (1.07 g, 8.7 mmol) was dissolved in a minimum amount of dry pyridine. Dicyclohexylcarbodiimide (1.97 g, 9.6 mmol) was dissolved in the mixture, with stirring. The solution was cooled to 0° C. and 4-aminobutanoic acid benzyl ester hydrochloride (2 g, 8.7 mmol) was added. After 30 minutes, the solution turned yellow and a precipitate was observed. Stirring was continued for 48 hours, after which time 1.8 g of dicyclohexylurea was removed from the yellow solution by filtration. The solution was evaporated to dryness and the residue was washed with 40 ml of ice cold water, extracted into ethyl acetate and dried over $Na_2SO_4$. Evaporation of solvent left the product as a sticky yellow oil. Identity of the product, which has the structural formula

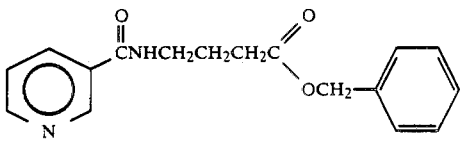

was confirmed by NMR analysis.

EXAMPLE 3

Preparation of 1-methyl-3{N-[(3'-benzyloxycarbonyl)propyl]}carbamoylpyridinium iodide (PR-28)

The product of Example 2 (0.92 g, 3.09 mmol) was dissolved in a minimum amount of acetone and cooled to 0° C. Methyl iodide (0.40 ml, 6.4 mmol) was added in one portion and the solution was slowly brought to the reflux temperature. The mixture was refluxed for 3 hours, then stirred overnight. Evaporation of solvent left a yellow oil which crystallized and which was recrystallized from acetone/ethyl ether. The light yellow crystals thus obtained were collected by filtration and dried. Anal. calc. for $C_{18}H_{21}N_2O_3I \cdot 1/8\ H_2O$: C, 48.86; H, 4.84; N, 6.33; I, 28.72. Found: C, 48.84; H, 4.81; N, 6.33; I, 28.94. UV $(\lambda^{max}) = 264, 236$ nm. NMR and IR analysis also confirmed the identity of the product, which has the structural formula

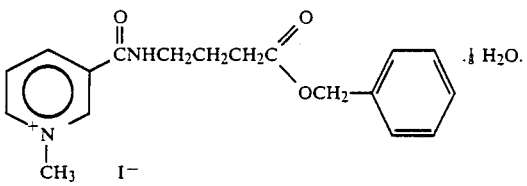

EXAMPLE 4

Preparation of 1-methyl-3{N-[(3'-benzyloxycarbonyl)propyl]}carbamoyl-1,4-dihydropyridine (PR-30)

The product of Example 3 (200 mg, 0.45 mmol) was dissolved in 20 ml deaerated water. Sodium bicarbonate (0.23 g, 6-fold excess) was added to the solution, with stirring. Sodium dithionite (0.31 d) was added and a yellow color was observed. Ethyl acetate (30 ml) was added and the mixture was stirred for 1½hours. The organic layer, containing the yellow dihydro compound, was separated from the aqueous layer and dried over $Na_2SO_4$. Evaporation of ethyl acetate left a yellow oil which reduced methanolic silver nitrate immediately. UV and NMR analysis confirmed the identity of the product, which has the formula

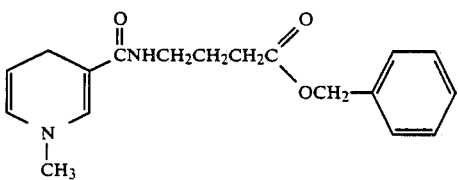

EXAMPLE 5

Preparation of 4-aminobutanoic acid cyclohexyl ester hydrochloride

GABA (8 g, 77.6 mmol) was suspended in 100 ml (0.96 mol) of cyclohexanol. Thionyl chloride (40 ml) was added dropwise to the mixture at 0° C. The mixture was then refluxed for 4 hours, cooled and crystallized from ethyl ether. The white crystals obtained in this manner were filtered and dried. NMR analysis confirmed the identity of the product.

EXAMPLE 6

Preparation of 3{N-L(3'-cyclohexyloxycarbonyl)propyl]}carbamoylpyridine

Nicotinic acid (2.2 g, 18 mmol) was suspended in 50 ml of dry pyridine. Dicyclohexylcarbodiimide (3.68 G, 17.9 mmol) was dissolved in the solution, with stirring. 4-Aminobutanoic acid cyclohexyl ester hydrochloride (4 g, 18 mmol) was added and the mixture was stirred for 48 hours. Precipitated dicyclohexylurea was removed by filtration and the filtrate was evaporated to dryness. The residue was washed with 25 ml of ice cold water and extracted into ethyl acetate. The layers were separated and the organic layer was evaporated to dryness. NMR analysis confirmed the structure of the product.

EXAMPLE 7

Preparation of 1-methyl-3{N-[(3'-Cyclohexyloxycarbonyl)propyl]}carbamoylpyridinium iodide The product of Example 6 (1.74 g, 6 mmol) was dissolved in a minimum amount of acetone and the resulting white precipitate was filtered. Methyl iodide (1.5 ml, 24 mmol) was added in one portion to the solution, with stirring, at 0° C. The mixture was allowed to gently reflux overnight. Filtration of a white precipitate and evaporation of the yellow filtrate produced a reddish oil, which was dissolved in acetone, filtered and evaporated to dryness. Anal. calc. for $C_{22}H_{23}O_3N_2I$: C, 47.26; H, 5.79; N, 6.48; I, 29.38. Found: C, 47.03; H, 5.85; N, 6.44; I, 29.26. The product has the formula

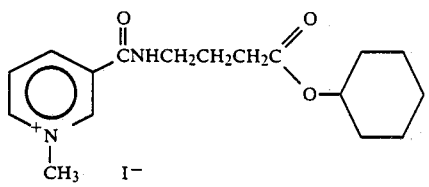

EXAMPLE 8

Preparation of 1-methyl-3{N-[(3'-cyclohexyloxycarbonyl)propyl]}carbamoyl-1,4-dihydropyridine The product of Example 7 (0.11 g, 0.26 mmol) was dissolved in 25 ml of ice cold deaerated water. $NaHCO_3$ (0.09 g, 4-fold excess) was added, followed by $Na_2S_2O_4$ (0.14 g, 3-fold excess). Ethyl acetate (25 ml) was added and the mixture was stirred under nitrogen for 30 minutes. The organic layer was extracted and dried to give an orange oil that reduced methanolic silver nitrate immediately. NMR analysis confirmed that the product has the structure:

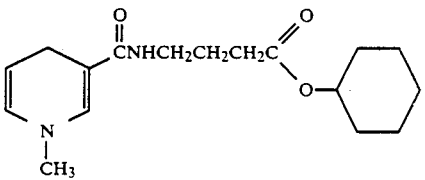

PHARMACOLOGICAL TESTING

Anxiolytic Study A

Male Sprague-Dawley rats were housed in temperature (26°±1° C.) and light (lights on 0500 to 1900 hours daily) controlled animal quarters for one week and then deprived of water for 48 hours and food for 24 hours. Groups of 5 to 9 rats were then administered, via a single intravenous (tail vein) injection, 4 mg/kg, 10 mg/kg or 25 mg/kg doses of 1-methyl-3{N-[(3'-benzyloxycarbonyl)propyl]}carbamoyl-1,4-dihydropyridine (PR-30), or of the vehicle, dimethylsulfoxide (DMSO). At 30 minutes and at 2, 4, 8 and 24 hours after administration, animals were tested for their anxiolytic responses. Since behavioral adaptation to the test was observed in initial studies, rats were used only once. The test consisted of presenting the water-deprived rats with 10% sucrose through a sipper. Animals were allowed 10 seconds of free drinking, then a 35 mA current was delivered to the sipper for 3 minutes and the drinking behavior of the animals was recorded on an event recorder. This test is a modification of that described by Vogel et al (Psychopharmacologica 21:1-7, 1971) in which higher numbers indicate a stronger anxiolytic response (i.e., a blockade of punished behavior). The data are summarized in Table I below.

TABLE I

Effects of Dose and Time on the Anxiolytic Response of Male Rats to PR-30, a Dihydropyridine Carrier System for GABA

| Time after Administration | | DMSO Control | PR-30 4 mg/kg | PR-30 10 mg/kg | PR-30 25 mg/kg |
|---|---|---|---|---|---|
| 30 minutes | Drinking Time (sec) | 24.5 ± 10.8 | 40.7 ± 15.0 | 64.8 ± 17.3 | 63.1 ± 20.8 |
| | Licks per 3 min period | 171.4 ± 75.6 | 285.0 ± 105.4 | 453.9 ± 121.4 | 441.7 ± 145.4 |
| 2 hours | Drinking Time (sec) | 10.8 ± 2.9 | 60.9 ± 9.9$^1$ | 84.1 ± 18.1$^1$ | 60.7 ± 13.8$^a$ |
| | Licks per 3 min period | 79.6 ± 20.3 | 426.3 ± 69.0$^a$ | 588.5 ± 126.6$^1$ | 424.7 ± 96.6$^a$ |
| 4 hours | Drinking Time (sec) | 8.5 ± 2.7 | 46.8 ± 14.3$^a$ | 48.6 ± 12.1$^a$ | 76.9 ± 18.3$^{a,b}$ |
| | Licks per 3 min period | 59.6 ± 19.1 | 327.9 ± 100.1$^a$ | 339.9 ± 84.8$^a$ | 538.4 ± 127.8$^{a,b}$ |
| 8 hours | Drinking Time (sec) | 6.4 ± 1.4 | 38.7 ± 11.1$^a$ | 60.2 ± 12.9$^a$ | 36.0 ± 12.4$^a$ |
| | Licks per 3 min period | 45.0 ± 9.4 | 271.0 ± 78.0$^a$ | 421.7 ± 90.3$^a$ | 252.3 ± 86.6$^a$ |
| 24 hours | Drinking Time (sec) | 8.0 ± 2.1 | 25.9 ± 12.9$^{a,c,d}$ | 5.7 ± 2.1 | 6.0 ± 2.4 |
| | Licks per 3 min period | 56.0 ± 14.3 | 181.6 ± 90.7$^{a,c,d}$ | 39.1 ± 14.8 | 42.0 ± 17.1 | a = $p < 0.05$ versus DMSO;
b = $p < 0.05$ versus 4 mg/kg;
c = $p < 0.05$ versus 10 mg/kg;
d = $< 0.05$ versus 25 mg/kg
All data are expressed as mean ± SEM.

From TABLE I, it can be seen that PR-30 produces a significant and prolonged anxiolytic effect at each dosage level tested. These conclusions are even more readily apparent from a consideration of FIG. 1, which is based on the same test results. In FIG. 1, the mean response (in number of licks during a three minute test period) at each dosage level is plotted against time; the mean response is represented by (●) for the DMSO-treated control rats, (○) for the rats treated with 4 mg/kg PR-30, (□) for the rats treated with 10 mg/kg PR-30 and (Δ) for the rats treated with 25 mg/kg PR-30. The vertical lines each represent 1 SEM. Differences among groups were evaluated for their significance by analysis of variance and Student-Newman-Keuls tests. a=p<0.05 versus DMSO; b=p<0.05 versus 4 mg/kg group; c=p<0.05 versus 10 mg/kg group; d=p<0.05 versus 25 mg/kg group.

Sedation Study

To estimate the sedative effects of PR-30, the effects of the drug on locomotor activity were studied in an open-field test.

Groups of male Sprague-Dawley rats having 10 animals per group were each administered, by single tail vein injection, one of the following: (a) DMSO vehicle; (b) 4 mg/kg PR-30; (c) 10 mg/kg PR-30; or (d) 25 mg/kg PR-30. Two hours later, the rats were placed in an open-field arena which was divided into 9 boxes, each 9" by 9". (The two hour time point was selected based on the results of ANXIOLYTIC STUDY A, in which maximum anxiolytic activity was observed at 2 hours at most dosage levels.) The number of boxes entered by an animal was counted each minute for five minutes as a measurement of locomotor activity.

Figure 2:
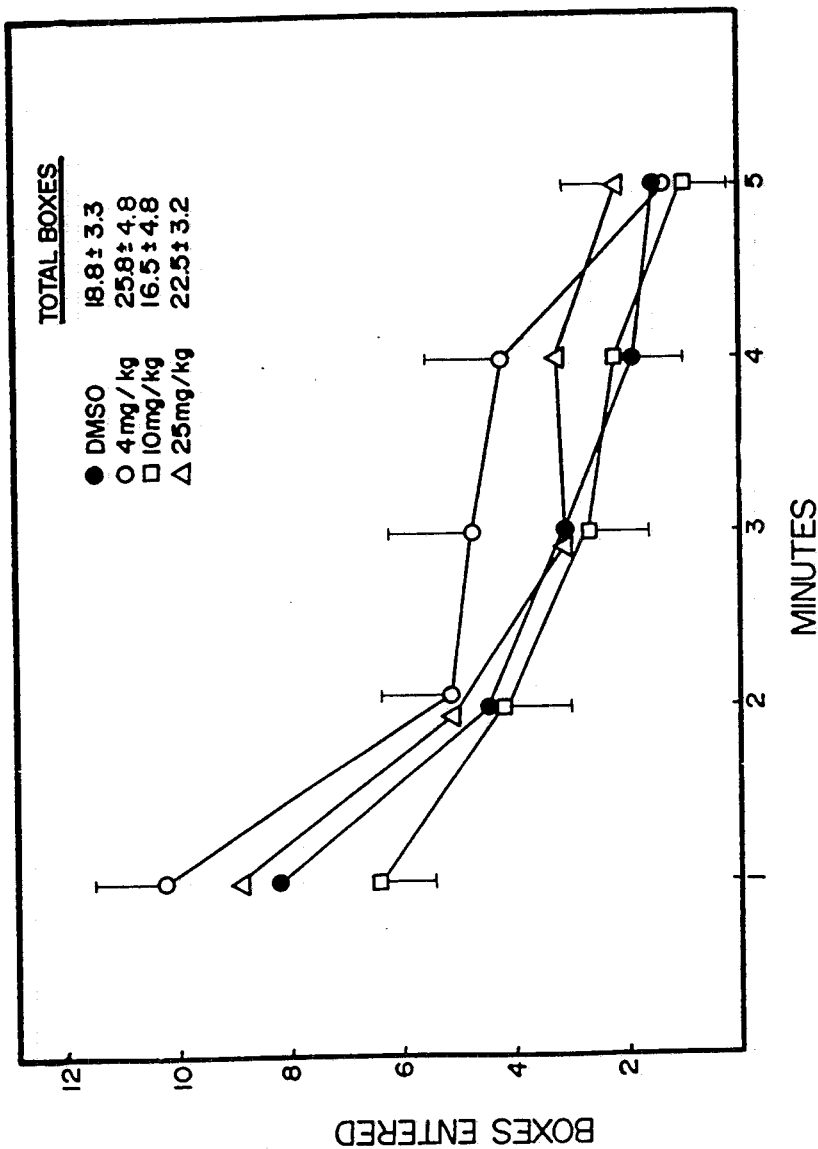
FIG. 2 is a plot of the mean number of boxes entered versus time from introduction into an open field arena, in a sedation study in groups of rats observed two hours after intravenous administration of dimethylsulfoxide vehicle (●) or of 4 mg/kg (○), 10 mg/kg (□) or 25 mg/kg (△) of PR-30.

FIG. 2 depicts the observed locomotor activity in terms of the mean number of boxes entered versus each time point (minutes 1 to 5) for each of the test groups. The symbols used are as defined in conjunction with FIG. 1. The table inserted in FIG. 2 represents the total activity of the animals during the five minute test period. To arrive at the total boxes indicated in the FIG. 2 table, in each test group the number of boxes entered by each animal during the entire test period was tallied, those numbers were totaled and the resulting mean and SEM were determined for each group. No significant difference (as evaluated by analysis of variance and Student-Newman-Keuls tests) was observed in total locomotor activity or in activity during any of the one minute sessions in the drug-treated groups as compared to controls, i.e. there was no evidence of sedation in any of the treatment groups.

Thus, a representative compound of formula (I) has been found to evoke a substantial anxiolytic response in rats at doses as low as 4 mg/kg while no sedation has been observed at doses as high as 25 mg/kg. Since doses lower than 4 mg/kg have not yet been tested, it is possible that doses significantly lower than 4 mg/kg will also elicit anxiolysis. It is also likely that doses substantially higher than 25 mg/kg can be administered without causing sedation.

Anxiolytic Study B

Adult male CD rats were purchased from the Charles Rivers Breeding Labs, Wilmington, MA, colony and housed in a temperature (26°±1° C.) and light (lights on 0500 to 1900 hours daily) controlled room. For about one week prior to experimentation, rats were provided with food and tap water ad libitum. Animals were then deprived of water for 48 hours and of food for 24 hours prior to administration by a single intravenous (iv) injection, via the tail vein, of one of the following: (a) the vehicle, dimethylsulfoxide (DMSO), 0.5 mg/kg; number of rats (n)=10; (b) γ-aminobutyric acid (GABA) 8.2 mg/kg; n=10; (c) the GABA-chemical delivery system, 1-methyl-3{N-[(3'-benzyloxycarbonyl)propyl]} carbamoyl-1,4-dihydropyridine (PR-30), 25 mg/kg; n=10) and (d) the quaternary ammonium form of the GABA delivery system, 1-methyl-3{N-[(3'-benzyloxycarbonyl)propyl]}carbamoylpyridinium iodide (PR-28), 35 mg/kg; n=9). GABA and PR-28 were administered in doses equimolar to that of PR-30. At exactly 4 hours after drug administration, animals were tested for their anxiolytic responses to the drugs. (The 4 hour time point was selected based on the results of ANXIOLYTIC STUDY A, in which 4 hours was the time at which the highest dose of PR-30, 25 mg/kg showed the largest response.) The test consisted of presenting the water deprived rats with a 10% sucrose solution through a sipper spout. After initiation of the drink, rats were allowed ten seconds of free drinking, at which time a 35 mA current was delivered continuously to the sipper for three minutes. The drinking behavior of the animals was recorded on an event recorder. In this test, a modification of that described by Vogel et al (Pharmacologica 21:1-7, 1971), a higher number indicates a stronger anxiolytic response.

The effects of the vehicle and test drugs on drinking behavior in this conflict test are presented in TABLE II below and in FIG. 3.

The results in terms of the mean response in drinking time and number of licks are set forth in TABLE III below.

TABLE III

Comparison of the Drinking Behavior of DMSO-treated and Untreated Control Animals under Shocked and Non-shocked Conditions.

|  | WITH SHOCK | | WITHOUT SHOCK | |
| --- | --- | --- | --- | --- |
|  | DMSO | CONTROL | DMSO | CONTROL |
| Drinking Time (sec) | 8.6 ± 2.7 | 13.3 ± 3.9 | 119.0 ± 8.2 | 115.1 ± 13.1 |
| Licks per 3 min period | 59.6 ± 19.1 | 93.1 ± 27.0 | 833.0 ± 57.7 | 805.5 ± 91.5 |

All data are expressed as mean ± SEM.

The test results were analyzed using a one way analysis of variance and Student-Newman-Keuls test, at a probability level of 0.05. There was no significant difference in results between DMSO-treated animals and untreated controls in the test mode employing shock.

TABLE II

Effects of γ-Aminobutyric Acid (GABA), a Dihydropyridine Carrier System for GABA (PR-30) and the Corresponding Quaternary Ammonium Form of the GABA Delivery System (PR-28) on Drinking Behavior in a Conflict Test

|  | DMSO Control | GABA | PR-28 | PR-30 |
| --- | --- | --- | --- | --- |
| Drinking Time (sec) | 5.3 ± 1.1[a] | 3.1 ± 0.5 | 3.3 ± 0.8 | 44.5 ± 5.7* |
| Licks per 3 min period | 36.9 ± 8.0 | 21.7 ± 3.3 | 23.3 ± 5.3 | 311.7 ± 40.1* |

[a] mean ± SEM
*p < 0.05 vs. all other groups

Figure 3:
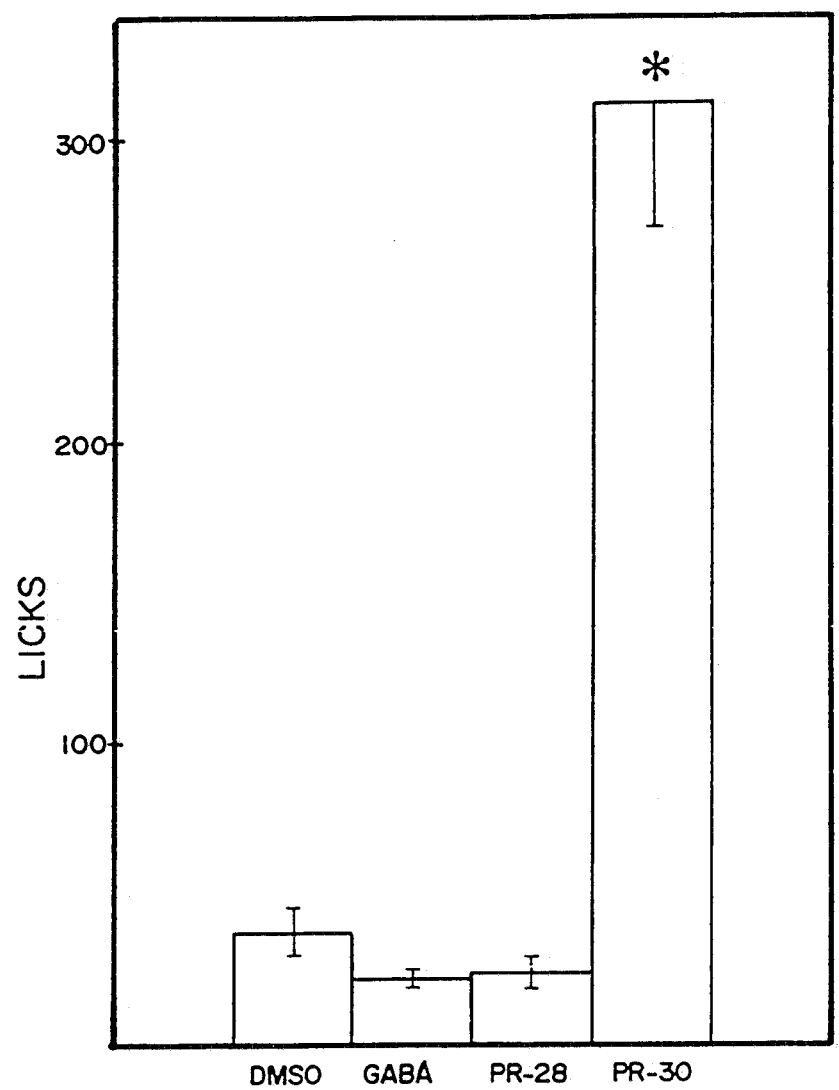
FIG. 3 is a bar graph illustrating the mean response in number of licks for dimethylsulfoxide (DMSO), γ-aminobutyric acid (GABA), 1-methyl-3{N-[(3'-benzyloxycarbonyl)propyl]}carbamoylpyridinium iodide (PR-28) and 1-methyl-3{N-[(3'-benzyloxycarbonyl)propyl]}carbamoyl-1,4-dihydropyridine (PR-30), in a punishment anxiolysis study in groups of rats four hours after intravenous administration of the vehicle or test compound.

FIG. 3 graphically illustrates the mean response, in number of licks during a three minute test period, tabulated above. The mean response in licks is depicted in the form of a bar graph for each of the treatment groups. The vertical line represents ±SEM.

As shown in TABLE II and FIG. 3, the dihydropyridine PR-30 caused an 8.4-fold increase in drinking time, indicating a dramatic anxiolytic effect of the drug. These results are consistent with ANXIOLYTIC STUDY A. In contrast, GABA and the quaternary PR-28 did not differ significantly from the control. The GABA and PR-28 results are consistent with the facts that (1) it is known that GABA itself, when administered systemically, does not cross the blood-brain barrier (BBB) to any appreciable extent and thus would not be expected to exert a central effect such as anxiolysis when administered in this test; and (2) the quaternary form of the carrier system is hydrophilic, not lipophilic, and thus would not be expected to cross the BBB to any significant extent; also, the Bodor patents teach that the "locked in" quaternary form is ideally inactive.

Control Study

It was of interest to determine if the DMSO vehicle used in the anxiolytic tests described above affected the test results in any way. To make that determination, the basic anxiolytic test procedure described above was repeated, but with the following changes:

(1) one group of rats received DMSO vehicle as before, while a second group of rats received nothing and served as the control group;

(2) two additional groups of rats were treated as in (1), but the test was modified to eliminate the shock delivered to the sipper, i.e. the punishment delivered in the usual anxiolytic test was not administered and the animals were able to drink freely without fear of shock during the entire test period.

The same was true in the unshocked test mode.

It can be concluded from this test that: (1) the drinking response in DMSO-treated rats as compared to non-treated rats is not significantly different under the usual punishment conditions; (2) under non-punishment/no shock conditions, DMSO does not affect unrestrained drinking behavior in rats; and (3) under unrestrained, normal conditions, rats drink for approximately 2 minutes of the 3 minute period.

Compositions for use in the method of this invention comprise an anxiolytically effective amount of a compound of formula (I) above or a non-toxic pharmaceutically acceptable salt thereof, and a non-toxic pharmaceutically acceptable carrier therefor.

Suitable non-toxic pharmaceutically acceptable carriers for use with the selected compound of formula (I) will be apparent to those skilled in the art of pharmaceutical formulation. See, for example, Remington's Pharmaceutical Sciences, seventeenth edition, ed. Alfonso R. Gennaro, Mack Publishing Company, Easton, Pennsylvania (1985). Obviously, the choice of suitable carriers will depend upon the exact nature of the particular dosage form selected, as well as upon the identity of the compound to be administered. The therapic dosage range for administration of a compound of formula (I) for use in eliciting anxiolysis can be estimated on the basis of animal test results detailed hereinabove. Naturally, such therapeutic dosage ranges will vary with the particular compound of formula (I) used, the size, species and condition of the subject, the severity of the subject's anxiety, the particular dosage form employed, the route of administration and the like. And the quantity of given dosage form needed to deliver the desired dose will of course depend upon the concentration of the compound of formula (I) in any given pharmaceutical composition/dosage form thereof. It is contemplated that parenteral dosage forms containing a compound of formula (I), e.g. those formulated for intravenous injection, will be particularly useful in the treatment of acute manifestations of extreme anxiety conditions, such as severe agitation, anxiety attacks, panic attacks and episodes of anxiety neurosis, or in other situations in which especially rapid onset of action is desired and/or in which a health care professional will administer the drug. On the other hand, for the chronic treatment of mild anxiety and/or the prevention of severe anxiety phases, a dosage form suitable for oral, sublingual, buccal or nasal administration is preferred.

The compounds of formula (I) exhibit prolonged activity. However, to further sustain action, the active ingredient may be formulated into a sustained release carrier system and/or a route of administration may be selected to slowly release the chemical, e.g. subcutaneous implantation.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims.

What we claim is:

1. A method of relieving anxiety without causing significant sedation in a mammal, said method comprising administering to a mammal in need of such treatment an anxiolytically effective, non-sedating amount of a compound of the formula

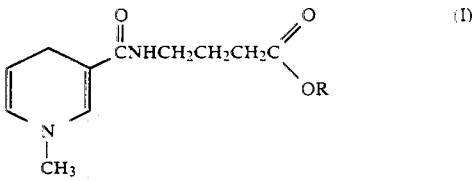

wherein R is benzyl or cyclohexyl, or a non-toxic pharmaceutically acceptable salt thereof.

2. A method of relieving anxiety without causing significant sedation in a mammal, said method comprising administering to a mammal in need of such treatment an anxiolytically effective, non-sedating amount of 1-methyl-3{N-[(3'-benzyloxycarbonyl)propyl]}carbamoyl-1,4-dihydropyridine or a non-toxic pharmaceutically acceptable salt thereof.

3. A method of relieving anxiety without causing significant sedation in a mammal, said method comprising administering to a mammal in need of such treatment a pharmaceutical composition in dosage unit form comprising, per dosage unit: (a) an anxiolytically effective, non-sedating amount of a compound of the formula

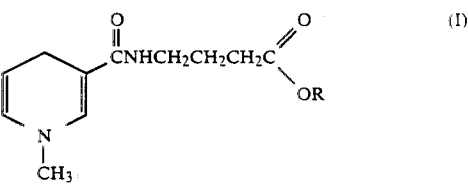

wherein R is benzyl or cyclohexyl, or a non-toxic pharmaceutically acceptable salt thereof; and (b) a non-toxic pharmaceutically acceptable carrier therefor.

4. A method according to claim 3, wherein (a) an anxiolytically effective, non-sedating amount of 1-methyl-3{N-[(3'-benzyloxycarbonyl)propyl]}carbamoyl-1,4-dihydropyridine.

* * * * *